United States Patent [19]

Aya et al.

[11] Patent Number: 4,552,586
[45] Date of Patent: Nov. 12, 1985

[54] CERTAIN 2-PYRIDYLOXYACETANILIDES AND THEIR USE AS HERBICIDES

[75] Inventors: Masahiro Aya; Junichi Saito; Kazuomi Yasui; Shinzo Kagabu; Atsumi Kamochi; Naoko Yamaguchi, all of Tokyo, Japan

[73] Assignee: Nihon Tokushu Noyaku Seizo K.K., Tokyo, Japan

[21] Appl. No.: 553,001

[22] Filed: Nov. 17, 1983

Related U.S. Application Data

[63] Continuation of Ser. No. 353,987, Mar. 2, 1982, abandoned.

[30] Foreign Application Priority Data

Mar. 12, 1981 [JP] Japan .................................. 56-34555

[51] Int. Cl.[4] .................... C07D 213/64; A01N 43/40
[52] U.S. Cl. ......................................... 71/94; 546/291
[58] Field of Search ............................. 546/291; 71/94

[56] References Cited

U.S. PATENT DOCUMENTS 4,110,104 8/1978 McGregor .
4,325,729 4/1982 Rempfler et al. ...................... 71/94
4,391,629 7/1983 Aya et al. ................................ 71/94

FOREIGN PATENT DOCUMENTS 2637886 3/1977 Fed. Rep. of Germany .
100306 7/1980 Japan .................................... 546/291
100307 7/1980 Japan .................................... 546/291
625940 10/1981 Switzerland .
1472485 5/1977 United Kingdom .

Primary Examiner—Alan L. Rotman
Attorney, Agent, or Firm—Sprung Horn Kramer & Woods

[57] ABSTRACT

2-Pyridyloxyacetanilides of the formula

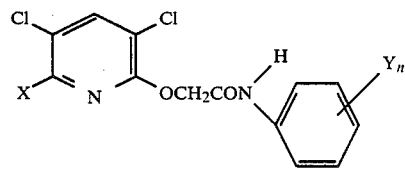

in which
X is hydrogen, $C_1$–$C_4$ alkyl or $C_1$–$C_4$ halogenoalkyl,
Y each independently is halogen, $C_1$–$C_4$ alkyl, $C_1$–$C_4$ alkoxy or $C_1$–$C_4$ halogenoalkyl, and
n is 0, 1, 2 or 3 which possess herbicidal and plant-growth regulating activity.

3 Claims, No Drawings

CERTAIN 2-PYRIDYLOXYACETANILIDES AND THEIR USE AS HERBICIDES

This is a continuation of application Ser. No. 353,987, filed Mar. 2, 1982, abandoned.

The present invention relates to certain new 2-pyridyloxyacetanilides, to a process for their preparation and to their use as herbicides.

British Patent Specification No. 1,472,485 discloses that 6-fluoro-3,5-dihalo-2-pyridyloxamide compounds of the general formula

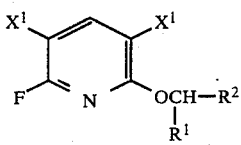
(A)

in which
$X^1$ is chloro, bromo or iodo,
$R^1$ is hydrogen or methyl, and
$R^2$ represents —$CONR^4R^4$ in which
$R^4$ represents hydrogen or alkyl having 1 to 8 carbon atoms,
have herbicidal activity.

Japanese Laid-open Patent Publication No. 100306/80 discloses an agent for controlling the shedding of fruit that contains an active ingredient the compound of 3,5,6-trichloro-2-pyridyloxacetic acid of the formula

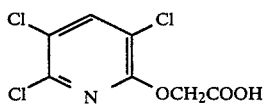
(B)

or its sodium salt, or its anilides. Japanese Laid-open Patent Publication No. 100307/80 discloses a fruit-thinning agent for use on tangerines, which agent contains the sodium salt or the anilides of the above formula (B). Neither of the aforesaid Japanese publications discloses specific examples of compounds other than the sodium salts. Furthermore, the salts disclosed therein are sprayed over the entire tree, especially over the fruits, in order to prevent the drop of the fruits. Alternatively, these salts are sprayed over the branches of the trees within 60 days after the maximum blooming period. Both the publications are completely silent on the herbicidal activity of the said salts.

The present invention now provides, as new compounds, the 2-pyridyloxyacetanilides of the general formula

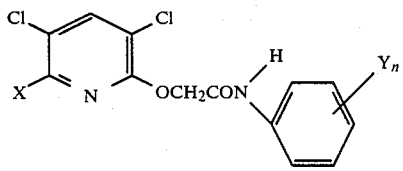
(I)

in which
X represents hydrogen, $C_1$–$C_4$ alkyl (that is methyl, ethyl, n- or isopropyl or n-, iso-, sec- or tert.-butyl) or $C_1$–$C_4$ halogenalkyl, Y represents halogen (that is fluorine, chlorine, bromine or iodine), $C_1$–$C_4$ alkyl, $C_1$–$C_4$ alkoxy (that is methoxy, ethoxy, n- or isopropoxy or n-, iso-, sec.- or tert.-butoxy) or $C_1$–$C_4$ halogenoalkyl, and
n is 0, 1, 2 or 3, the substituents Y being selected independently when n is 2 or 3.

The invention also provides a process for the preparation of a compound of the formula (I), in which a 2-pyridyloxy acetic acid of the general formula

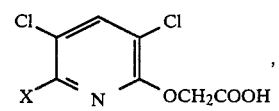
(II)

in which
X has the meaning given above, and an aniline of the general formula

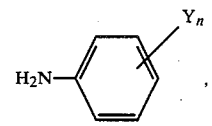
(III)

in which
Y and n have the meanings given above are condensed dehydratively.

It has been found that the compounds of the formula (I) have an excellent herbicidal activity and a broad spectrum of action. They also have a very low toxicity towards warm-blooded animals.

The compounds of the present invention have shown a greater herbicidal activity in tests than certain herbicidal compounds disclosed in the prior art. The present invention therefore represents an enrichment of the art.

Preferred compounds of the formula (I) are those in which
X represents hydrogen, methyl, mono-, di- or trichloromethyl or mono-, di- or trifluoromethyl,
Y represents fluorine, chlorine, bromine, methyl, ethyl, n-propyl, isopropyl, methoxy, ethoxy, n-propoxy, isopropoxy, mono, di- or trichloromethyl or mono-, di- or trifluoromethyl, and
n is 0, 1 or 2.

Examples of the compounds of this invention are:
3,5-dichloro-2-pyridyloxyacetoanilide, 3,5-dichloro-2-pyridyloxyaceto-2-(or 3- or 4-)chloroanilide, 3,5-dichloro-6-methyl-2-pyridyloxyacetoanilide, 3,5-dichloro-2-pyridyloxyaceto-2-(or 3- or 4-)bromanilide, 3,5-dichloro-2-pyridyloxyaceto-2-(or 3- or 4-)-fluoranilide, 3,5-dichloro-2-pyridyloxyaceto-2-(or 3- or 4-)methylanilide, 3,5-dichloro-2-pyridyloxyaceto-2-(or 3- or 4-)ethylanilide, 3,5-dichloro-2-pyridyloxyaceto-2-(or 3- or 4-)propylanilide, 3,5-dichloro-2-pyridyloxyaceto-2-(or 3- or 4-)iso-propylanilide, 3,5-dichloro-2-pyridyloxyaceto-2-(or 3- or 4-)methoxyanilide, 3,5-dichloro-2-pyridyloxyaceto-2-(or 3- or 4-)-ethoxyanilide, 3,5-dichloro-2-pyridyloxyaceto-2-(or 3- or 4-)isopropoxyanilide, 3,5-dichloro-2-pyridyloxyaceto-2-(or 3- or 4-)-trifluoromethylanilide, 3,5-dichloro-2-pyridyloxyaceto-2,4-(or 2,6-)dichloranilide, 3,5-dichloro-2-pyridyloxyaceto-2,4,5-(or 2,4,6)-trichloranilide, 3,5-dichloro-2-pyridyloxyaceto-2,3-dimethylanilide, 3,5-dichloro-2-pyridyloxyaceto-2,4-dimethylanilide, 3,5-dichloro-6-trifluoromethyl-2-pyridyloxyacetanilide, and 3,5-dichloro-6-trichloromethyl-2-pyridyloxyacetoanilide.

If 3,5-dichloro-6-methyl-2-pyridyloxyacetic acid and aniline are used as starting materials in process of the present invention, the course of the reactions may be represented by the following equations:

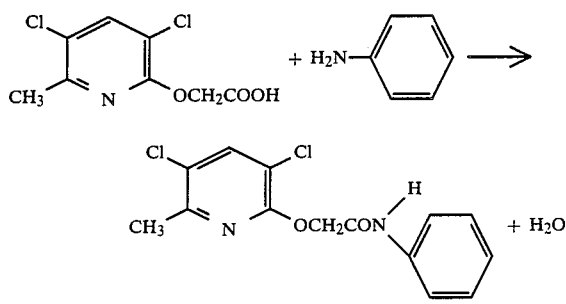

Examples of the 2-pyridyloxy acetic acid of the formula (II), which can be used as starting materials in the process of the present invention, include:

3,5-dichloro-2-pyridyloxy acetic acid, 3,5-dichloro-6-methyl-2-pyridyloxy acetic acid, 3,5-dichloro-6-ethyl-2-pyridyloxy acetic acid, 3,5-dichloro-6-n-(or iso-)propyl-2-pyridyloxy acetic acid, 3,5-dichloro-6-n-(or iso-, sec- or tert-)butyl-2-pyridyloxy acetic acid, 3,5-dichloro-6-chloromethyl-(or dichloromethyl or trichloromethyl)-2-pyridyloxy acetic acid, or 3,5-dichloro-6-fluoromethyl(or difluoromethyl or trifluoromethyl)-2-pyridyloxy acetic acid.

Examples of the aniline of the formula (III), which can also be used as starting materials in the process of the present invention, include:

aniline, 2-(or 3- or 4-)chloraniline, 2-(or 3- or 4-)bromaniline, 2-(or 3- or 4-)fluoraniline, 2-(or 3- or 4-)methylaniline, 2-(or 3- or 4-)-ethylaniline, 2-(or 3- or 4-)propyl-(or iso-propyl-)aniline, 2-(or 3- or 4-)-n-butyl-(or iso-, sec- or tert-butyl-)aniline, 2-(or 3- or 4-)methoxyaniline, 2-(or 3- or 4-)ethoxyaniline, 2-(or 3- or 4-)propoxy-(or iso-propoxy-)aniline, 2-(3- or 4-)-n-butoxy-(or iso-, sec- or tert-butoxy-)aniline, 2-(or 3- or 4-)chloromethyl-(or dichloromethyl- or trichloromethyl-)aniline, 2-(or 3- or 4-)fluoromethyl-(or difluoromethyl- or trifluoromethyl-)aniline, 2,4-(or 2,6-)dichloroaniline, 2,3-(or 2,4-)dimethylaniline, or 2,4,5-(or 2,4,6-)trichloroaniline.

The process of the present invention is preferably carried out using a solvent or a diluent. For this purpose, any inert solvent or diluent can be used.

Examples of such solvents or diluents include water; aliphatic, alicyclic and aromatic hydrocarbons (optionally chlorinated), such as hexane, cyclohexane, petroleum ether, ligroin, benzene, toluene, xylene, methylene chloride, chloroform, carbon tetrachloride, ethylene chloride, trichloroethylene and chlorobenzene; ethers such as diethyl ether, methyl ethyl ether, di-isopropyl ether, dibutyl ether, propylene oxide, dioxane and tetrahydrofuran; ketones such as acetone, methyl ethyl ketone, methyl isopropyl ketone and methyl isobutyl ketone; nitriles such as acetonitrile, propionitrile and acrylonitrile; alcohols such as methanol, ethanol, isopropanol, butanol and ethylene glycol; esters such as ethyl acetate and amyl acetate; acid amides such as dimethyl formamide and dimethyl acetamide; sulfones and sulfoxides such as dimethyl sulfoxide and sulfolane; and bases such as pyridine.

Of course, a mixture of solvents and/or diluents could be used.

The dehydrative condensation reaction in the process of the present invention may be carried out at a high temperature, generally between about 100° C. and about 200° C., preferably between a melting point of the mixture and 200° C., or by removing water which was formed in the reaction system by azeotropic distillation, or in the presence of a condensing agent. Examples of such condensing agent are carbodiimides, enamines or tetrachlorosilicate.

The active compounds according to the invention influence plant growth and can therefore be used as defoliants, desiccants, agents for destroying broad-leaved plants, germination inhibitors and, especially, as weedkillers. By "weeds" in the broadest sense there are meant plants growing in places where they are not desired.

Whether the compounds according to the invention act as total herbicides or selective herbicides depends essentially on the amount used.

The active compounds according to the present invention may be used, for example, to combat the following plants:

dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monocharia, Fimbristylis, Sagittaria, Eleocharis, Scirpus, Paspalum, Ischaemum, Spenoclea, Dactyloctenium, Agrostis, Alopecurus and Apera.

The active compounds according to the present invention may be used, for example, as selective herbicides in the following cultures:

dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and monocotyledon cultures of the genera Oryza, Zea, Triticum, Hordeum, Avena, Secale, Sorghum, Panicum, Saccharum, Ananas, Asparagus and Allium.

However, the use of the active compounds according to the invention is in no way restricted to these genera but also embraces other plants, in the same way.

Depending on the concentrations, the compounds can be used for the total combating of weeds, for example on industrial terrain and railway tracks and on paths and squares with or without trees. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annual cultures.

The present compounds are very effective when used to combat weeds occurring in paddy fields and show substantially no phytotoxicity to the rice plants being cultivated. The compounds can be used before, during and after the emergence of the weeds. They can be applied for example to the soil and/or to the stems and leaves of the weeds. As examples of paddy-field weeds there may be mentioned *Rotala indica, Lindernia procumbens, Ludwiga prostrata, Potamogeton distinctus, Elatine triandra, Echinochloa crus-galli, Monochoria vaginalis, Eleocharis acicularis, Eleocharis kuroguwai, Cyperus difformis, Cyperus serotinus, Sagittaria pygmaea, Alisma canaliculatum* and *Scirpus juncoides.*

The active compounds can be converted into the customary formulations, such as solutions, emulsions, wettable powders, suspensions, dusting agents, pastes, soluble powders, granules, suspension-emulsion concentrates, natural and synthetic materials impregnated with active compound, and very fine capsules in polymeric substances.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.01 to 100 percent by weight of active compound, preferably from 0.05 to 95 percent by weight.

The active compounds according to the invention, as such or in the form of their formulations, can also be used, for combating weeds, as mixtures with known herbicides, finished formulations or tank mixing being possible. Mixtures with other known active compounds, such as fungicides, insecticides, acaricides, nematicides, bird repellents, growth factors, plant nutrients and agents which improve soil structure, are also possible.

By including other active ingredients, it is possible to obtain a broad herbicidal spectrum and an accurate control effect; a synergistic effect by mixing of these is also expected. Examples of the other active ingredients include:

benzothiazol-2-yloxyaceto-N,N-diallyamide, benzoxazol-2-yloxyaceto-N-sec-butyl-N-methylamide, benzoxazol-2-yloxyaceto-N-cyclohexyl-N-methylamide, benzothiazol-2-yloxyaceto-N-methyl-N-(1-methylpropargyl)amide, benzoxazol-2-yloxyaceto-N-benzyl-N-propargylamide, benzothiazol-2-yloxyaceto-2'-ethylpiperidide, benzothiazol-2-yloxy-aceto-2',4'-dimethylpiperidide, benzoxazol-2-yloxyaceto-2',4',6'-trimethylpiperidide, benzoxazol-2-yloxyaceto-hexamethyleneimide, benzothiazol-2-yloxyaceto-perhydroindolide, benzoxazol-2-yloxyaceto-perhydroindolide, benzothiazol-2-yloxyaceto-1',2',3',4'-tetrahydroquinolide, benzoxazol-2-yloxyaceto-2'-methyl-1',2',3',4'-tetrahydroquinolide, benzoxazol-2-yloxyaceto-N-methylanilide, benzothiazol-2-yloxyaceto-N-methylanilide, benzoxazol-2-yloxyaceto-N-ethylanilide, benzoxazol-2-yloxyaceto-N-isopropylanilide, benzoxazol-2-yloxyaceto-N-propylanilide, benzothiazol-2-yloxyaceto-N-methyl-N-2'-methoxyanilide, benzoxazol-2-yloxyaceto-N-methyl-N-2'-methoxyanilide, benzoxazol-2-yloxyaceto-N-methyl-N-2'-trifluoromethylanilide, benzothiazol-2-yloxyaceto-N-methyl-N-2'-chloroanilide, benzoxazol-2-yloxyaceto-N-methyl-N-2'-chloranilide, benzothiazol-2-yloxy-aceto-N-methyl-N-2'-fluoranilide, benzoxazol-2-yloxyaceto-N-methyl-N-2'-fluoranilide, benzothiazol-2-yloxyaceto-N-methyl-N-3'-methylanilide, benzoxazol-2-yloxyaceto-N-methyl-N-3'-methylanilide, benzothiazol-2-yloxyaceto-N-methyl-N-3'-methoxyanilide, benzoxazol-2-yloxyaceto-N-methyl-N-3'-methoxyanilide, benzothiazol-2-yloxyaceto-N-methyl-N-3'-isopropoxyanilide, benzothiazol-2-yloxyaceto-N-methyl-N-3'-trifluoromethylanilide, benzoxazol-2-yloxyaceto-N-methyl-N-3'-trifluoromethylanilide, benzothiazol-2-yloxyaceto-N-methyl-N-3'-chloranilide, benzoxazol-2-yloxyaceto-N-methyl-N-3'-chloranilide, benzothiazol-2-yloxyaceto-N-methyl-N-3'-fluoranilide, benzoxazol-2-yloxyaceto-N-methyl-N-3'-fluoranilide, benzothiazol-2-yloxyaceto-N-methyl-N-3'-bromanilide, benzoxazol-2-yloxyaceto-N-methyl-N-3'-bromanilide, benzoxazol-2-yloxyaceto-N-methyl-N-4'-methylanilide, benzoxazol-2-yloxyaceto-N-methyl-N-4'-methoxyanilide, benzoxazol-2-yloxyaceto-N-methyl-N-4'-fluoranilide, benzoxazol-2-yloxyaceto-N-methyl-N-2',3'-dimethylanilide, benzoxazol-2-yloxyaceto-N-methyl-N-2',3'-dichloranilide, benzoxazol-2-yloxyaceto-N-methyl-N-4'-chloro-2'-methylanilide, benzothiazol-2-yloxyaceto-N-methyl-N-2',5'-dichloranilide, benzoxazol-2-yloxyaceto-N-methyl-N-2',5'-dichloranilide, benzothiazol-2-yloxyaceto-N-methyl-N-3',5'-dimethylanilide, benzoxazol-2-yloxyaceto-N-methyl-N-3',5'dimethylanilide, benzoxazol-2-yloxyaceto-N-methyl-N-3',5'-di-trifluoromethyl-anilide, benzoxazol-2-yloxyaceto-N-methyl-N-5'-indanylamide, benzothiazol-2-yloxyaceto-N-methyl-N-3'-ethylanilide, benzoxazol-2-yloxyaceto-N-methyl-N-3'-ethylanilide, benzothiazol-2-yloxyaceto-N-isopropylanilide, 2-chloro-2',6'-diethyl-N-(butoxymethyl)-acetanilide, 2-chloro-2',6'-diethyl-N-(n-propoxyethyl)-acetanilide, N-(O,O-dipropyl-dithiophosphorylacetyl)-2-methyl-piperidine, S-(4-chlorobenzyl)-N,N-diethylthiolcarbamate, S-ethyl-N,N-hexamethylenethiolcarbamate, O-methyl-O-(2-nitro-p-tolyl)-N-isopropylphosphoramide thioate, O-ethyl-O-(2-nitro-5-methylphenyl)-N-sec.-butylphosphoramide thioate, benzoxazol-2-yloxyaceto-N-methyl-N-3'-isopropoxyanilide, 3,4-dimethyl-2,6-dinitro-N-1-ethylpropylaniline, α,α,α,-trifluoro-2,6-dinitro-N,N-dipropyl-p-toluidine, 4,5-dichloro-1,3-thiazol-2-yloxyaceto-N-isopropyl-N-ethoxyethoxyamide, and 5-ethyl-1,3,4-thiadiazol-2-yloxyaceto-1',2',3',4'-tetrahydroquinolide.

The active compounds can be used as such, in formulations thereof or in the use forms prepared therefrom by further dilution, such as ready-to-use solutions, suspensions, emulsions, powders, pastes and granules. They are used in the customary manner, for example by watering, spraying, atomizing, scattering or dusting.

The amount of active compound in the ready-to-use preparations can vary widely according to circumstances. However, it is in general form 0.01 to 95 percent, preferably from 0.05 to 60 percent by weight.

The active compounds can be applied after emergence of the plants, but are preferably applied before emergence of the plants, that is to say by the pre-emergence method. They can also be incorporated into the soil before sowing.

The amount of active compound used can vary within a substantial range. It depends essentially on the nature of the desired effect. In general, the amounts used are between 0.1 and 3 kg of active compound per hectare, preferably between 0.2 and 1 kg/ha.

The present invention also provides herbicidal or plant-growth regulating compositions containing as active ingredient a compound of the present invention in admixture with a solid diluent or carrier or in admixture with a liquid diluent or carrier containing a surface-active agent.

The present invention also provides a method of combating weeds which comprises applying to the weeds, or to a habitat thereof, a compound of the present invention alone or in the form of a composition containing as active ingredient a compound of the present invention in admixture with a diluent or carrier.

The present invention also provides a method of regulating the growth of plants which comprises applying to the plants, or to a habitat thereof, a compound of the present invention alone or in the form of a composition containing as active ingredient a compound of the present invention in admixture with a diluent or carrier.

The present invention further provides crops protected from damage by weeds by being grown in areas in which immediately prior to and/or during the time of the growing a compound of the present invention was applied alone or in admixture with a diluent or carrier.

The present invention further provides plants, the growth of which has been regulated by their being grown in areas in which immediately prior to and/or during the time of the growing a compound of the present invention was applied alone or in admixture with a diluent or carrier.

It will be seen that the usual methods of providing a harvested crop may be improved by the present invention.

The following example serves to illustrate the invention further.

PREPARATIVE EXAMPLE

Example 1

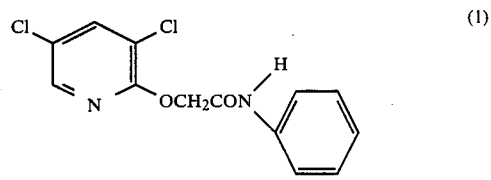

2.22 g of 3,5-dichloro-2-pyridyloxy acetic acid was suspended in 30 ml of toluene, and 2.06 g of N,N'-dicyclohexylcarbodiimide was added. The mixture was stirred for 15 minutes. To this solution, 0.93 g of aniline dissolved in 5 ml of toluene was added dropwise. The reaction was slightly exothermic, and stirring is continued at room temperature for 2 hours. The reaction mixture was then filtered. After removing the toluene from the filtrate by distillation under reduced pressure, the residue was washed with a small amount of ethanol to give 2.52 g of 3,5-dichloro-2-pyridyloxyacetanilide (Yield 85%), m.p. 164.5°~166° C.

The compounds shown in Table 1 were obtained by method analogous to that described in the preceding example.

TABLE 1

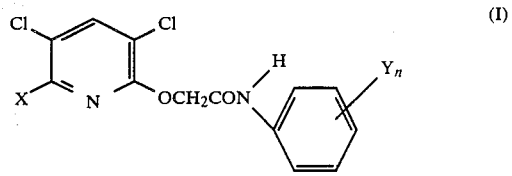

| Compound No. | X | Yn | m.p. |
| --- | --- | --- | --- |
| 2 | CH$_3$ | — | 109.5–110.5° C. |
| 3 | H | 2-F | 146–149° C. |
| 4 | H | 4-Cl | 153–154° C. |
| 5 | H | 2-CH$_3$ | 164–165° C. |
| 6 | H | 3-CH$_3$ | 140–141° C. |
| 7 | CH$_3$ | 4-CH$_3$ | 137–138° C. |
| 8 | H | 4-iso-C$_3$H$_7$ | 155–156° C. |
| 9 | H | 3-CF$_3$ | 94–100° C. |
| 10 | H | 2-CH$_3$O— | 139–140° C. |
| 11 | CH$_3$ | 4-CH$_3$O— | 100–105° C. |
| 12 | H | 2-iso-C$_3$H$_7$O— | 127–129° C. |
| 13 | CH$_3$ | 2,5-Cl$_2$ | 166–170° C. |
| 14 | H | 3,4-Cl$_2$ | 168–169° C. |
| 15 | H | 2,3-(CH$_3$)$_2$ | 175–176° C. |
| 16 | H | 2-CH$_3$—4-Cl | 166–167° C. |

Compositions according to this invention are illustrated in the following examples.

In these examples, the compounds according to the present invention are each identified by the number (given in brackets) of the corresponding preparative example.

Example 2

Fifteen parts of compound (1), 80 parts of a 1:5 mixture of powdery diatomaceous earth and powdery clay, 2 parts of sodium alkylbenzenesulfonate and 3 parts of sodium alkylnaphthalenesulfonate/formaldehyde condensate were pulverized and mixed to form a wettable powder. The wettable powder was diluted with water before use.

Example 3

Thirty parts of compound (2), 55 parts of xylene, 8 parts of polyoxyethylene alkylphenyl ether and 7 parts of calcium alkylbenzenesulfonate were mixed with stirring to form an emulsifiable concentrate. The emulsifiable concentrate was diluted with water before use.

Example 4

Two parts of compound (3) and 98 parts of powdery clay were pulverized and mixed to form a dusting agent.

Example 5

Compound (4) (1.5 parts), 0.5 part of isopropyl hydrogen phosphate (PAP) and 98 parts of powdery clay were pulverized and mixed to form a dusting agent.

Example 6

Water (25 parts) was added to a mixture of 10 parts of compound (5), 30 parts of bentonite (montmorillonite), 58 parts of talc and 2 parts of ligninsulfonate salt, and they were well kneaded. The mixture was formed into granules having a size of 10 to 40 mesh by means of an extrusion-type granulator, and dried at 40° to 50° C. to form granules.

Example 7

A rotary mixer was charged with 95 parts of clay mineral particles having a particle size distribution in the range of 0.2 to 2 mm, and, while rotating the mixer, 6.5 parts of compound (6) dissolved in an organic solvent were sprayed uniformly onto the clay mineral particles. The particles were then dried at 40° to 50° C. to form granules.

The herbicidal activity of the compounds of this invention is illustrated by the following examples wherein the compounds according to the present invention are each identified by the number (given in brackets) from Example 1 and Table 1 hereinabove.

The known comparison compounds are identified as follows:

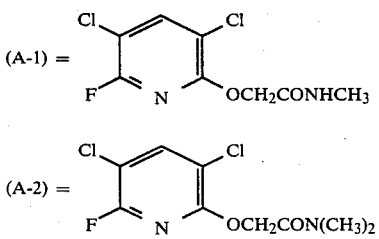

These compounds are disclosed in GB-PS No. 1,472,485.

Example 8

Test against aquatic paddy-field weeds by treating the soil and stalks and leaves under irrigation conditions (pot test)

Preparation of an active compound

Carrier: 5 parts by weight of acetone

Emulsifier: 1 part by weight of benzyloxy polyglycol ether

A preparation of the active compound was obtained as an emulsifiable concentrate by mixing 1 part of the active compound and the aforesaid amounts of the carrier and emulsifier. A predetermined amount of the preparation was obtained by dilution with water.

Test Procedure

Wagner pots (1/5,000 are) were filled with paddy-field soil, and two rice seedlings (variety: Kinmaze) were transplanted in each pot. Seeds of *Echinochloa crus-galli*, *Cyperus iria*, *Monochoria vaginalis*, *Scirpus juncoides* and certain broad-leaved weeds, small pieces of *Eleocharis acicularis* and tubers of *Cyperus serotinus* and *Sagittaria pygmaea* were put into the pots, and the pots were maintained in a wet condition. When *Echinochloa crus-galli* had grown to approximately the two-leaf stage (about 7 to 9 days after the sowing), the pots were filled with water to a depth of about 6 cm, and a predetermined amount of the active compound in the form of an emulsion was applied by means of a pipette. After the treatment, the water was allowed to leak from the pots at a rate of 2 to 3 cm per day for two days. Then, the depth of water in the pots was maintained at about 3 cm, and four weeks after the treatment with the active compound, the herbicidal effect and the degree of phytotoxicity were evaluated on a scale of from 0 to 5 in accordance with the following standards.

The effects were evaluated as follows in comparison with an untreated control.

| Rating | Weed-kill ratio based on the control |
|--------|--------------------------------------|
| 5 | at least 95% (withered) |
| 4 | at least 80% but less than 95% |
| 3 | at least 50% but less than 80% |
| 2 | at least 30% but less than 50% |
| 1 | at least 10% but less than 30% |
| 0 | less than 10% (not effective) |

The phytotoxicity towards the rice plants was evaluated as follows in comparison with the untreated control.

| Rating | Phytotoxicity rate in comparison with the control |
|--------|---------------------------------------------------|
| 5 | at least 90% (fatal damage) |
| 4 | at least 50% but less than 90% |
| 3 | at least 30% but less than 50% |
| 2 | at least 10% but less than 30% |
| 1 | more than 0 but less than 10% |
| 0 | 0% (no phytotoxity) |

The test results are shown in Table 2 in which the symbols A to H represent the following weeds:
A: *Echinochloa crus-galli* Beauv. var
B: *Eleocharis acicularis* L.
C: *Cyperus iria* L.
D: *Scirpus juncoides* Roxburgh var.
E: *Monochoria vaginalis* Presl.
F: broad-leaved weeds (including *Lindernia procumbens* Philcox, *Rotala indica* Koehne, *Elatine triandra* Schk).
G: *Cyperus serotinus* Rottboel
H: *Sagittaria pygmaea* Mig.

TABLE 2

| Compound | Amount of the active ingredient kg/ha | Herbicidal effect | | | | | | | | Phytotoxicity on rice |
|---|---|---|---|---|---|---|---|---|---|---|
| | | A | B | C | D | E | F | G | H | |
| (1) | 0.5 | 5 | 5 | 5 | 5 | 5 | 5 | 5 | 5 | 0 |
| (2) | 0.5 | 5 | 5 | 5 | 5 | 5 | 5 | 5 | 5 | 0 |
| (3) | 0.5 | 5 | 5 | 5 | 5 | 5 | 5 | 5 | 5 | 0 |
| (4) | 0.5 | 5 | 5 | 5 | 5 | 5 | 5 | 5 | 5 | 0 |
| (5) | 0.5 | 5 | 5 | 5 | 5 | 5 | 5 | 5 | 5 | 0 |
| (6) | 0.5 | 5 | 5 | 5 | 5 | 5 | 5 | 5 | 5 | 0 |
| (7) | 0.5 | 5 | 5 | 5 | 5 | 5 | 5 | 5 | 5 | 0 |
| (8) | 0.5 | 5 | 5 | 5 | 5 | 5 | 5 | 5 | 5 | 0 |
| (9) | 0.5 | 5 | 5 | 5 | 5 | 5 | 5 | 5 | 5 | 0 |
| (10) | 0.5 | 5 | 5 | 5 | 5 | 5 | 5 | 5 | 5 | 0 |
| (11) | 0.5 | 5 | 5 | 5 | 5 | 5 | 5 | 5 | 5 | 0 |
| (12) | 0.5 | 5 | 5 | 5 | 5 | 5 | 5 | 5 | 5 | 0 |
| (13) | 0.5 | 5 | 5 | 5 | 5 | 5 | 5 | 5 | 5 | 0 |
| (14) | 0.5 | 5 | 5 | 5 | 5 | 5 | 5 | 5 | 5 | 0 |
| (15) | 0.5 | 5 | 5 | 5 | 5 | 5 | 5 | 5 | 5 | 0 |
| (16) | 0.5 | 5 | 5 | 5 | 5 | 5 | 5 | 5 | 5 | 0 |
| (A-1) | 0.5 | 2 | 4 | 4 | 2 | 3 | 4 | 2 | 3 | 0 |
| (A-2) | 0.5 | 1 | 1 | 4 | 1 | 1 | 3 | 1 | 1 | 0 |

It will be appreciated that the instant specification and examples are set forth by way of illustration and not limitation, and that various modifications and changes may be made without departing from the spirit and scope of the present invention.

We claim:

1. In the cultivation of rice the method of combating weeds which comprises applying to the rice or to a field in which the rice is grown or to be grown a herbicidally effective amount of a 2-pyridyloxyacetanilide of the formula

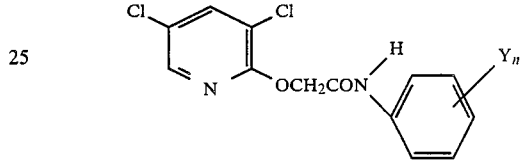

in which
Y each independently is $C_1$–$C_4$-alkyl or $CF_3$, and
n is 0, 1, 2 or 3.

2. A method according to claim 1, in which
Y each independently is methyl, ethyl, n-propyl, isopropyl or $CF_3$.

3. A method according to claim 1, wherein the 2-pyridyloxyacetanilide is 3,5-dichloro-2-pyridyloxyacetanilide of the formula

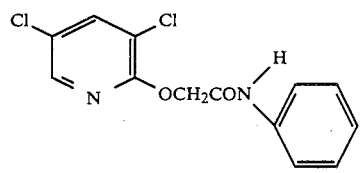

* * * * *